(12) United States Patent
Nakano (10) Patent No.: US 9,311,547 B2
(45) Date of Patent: Apr. 12, 2016

(54) FAILURE DETECTION SYSTEM AND FAILURE DETECTION METHOD

(75) Inventor: Takumi Nakano, Kagawa (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 14/130,151

(22) PCT Filed: Jun. 29, 2012

(86) PCT No.: PCT/JP2012/004259
§ 371 (c)(1),
(2), (4) Date: Mar. 24, 2014

(87) PCT Pub. No.: WO2013/005407
PCT Pub. Date: Jan. 10, 2013

(65) Prior Publication Data
US 2014/0198971 A1    Jul. 17, 2014

(30) Foreign Application Priority Data
Jul. 1, 2011    (JP) .................................. 2011-147783

(51) Int. Cl.
*G06K 9/00*   (2006.01)
*G06K 9/20*   (2006.01)
*A61F 13/15*  (2006.01)

(52) U.S. Cl.
CPC ........ *G06K 9/2054* (2013.01); *A61F 13/15772* (2013.01)

(58) Field of Classification Search
None
See application file for complete search history.

(56) References Cited

U.S. PATENT DOCUMENTS

| 6,266,436 | B1 | 7/2001 | Bett et al. | |
| 7,174,774 | B2* | 2/2007 | Pawar et al. | 73/73 |
| 7,809,179 | B2* | 10/2010 | Singh et al. | 382/141 |
| 2004/0064115 | A1* | 4/2004 | Arora et al. | 604/361 |
| 2007/0217672 | A1* | 9/2007 | Shannon et al. | 382/152 |
| 2013/0062263 | A1* | 3/2013 | Nakano | 209/552 |
| 2013/0304246 | A1* | 11/2013 | Rosani et al. | 700/110 |

FOREIGN PATENT DOCUMENTS

| CN | 201434842 Y | 3/2010 |
| JP | 5-82422 | 11/1993 |
| JP | 10-263010 | 10/1998 |
| JP | 2002-535040 A | 10/2002 |

(Continued)

OTHER PUBLICATIONS

Chinese Office Action and English translation from corresponding Chinese Application No. 201280031559.X dated Sep. 29, 2014 (14 pgs).

(Continued)

*Primary Examiner* — Daniel Mariam
(74) *Attorney, Agent, or Firm* — Brinks Gilson & Lione (57) ABSTRACT

A failure detection system that includes an image processing unit configured to acquire a morphological image illustrating a morphology of the absorbent article after processing of the absorbent article, in each of the plurality of steps, a failure detection unit configured to detect the existence of a failure location of the absorbent article after processing, based on the morphological image acquired by the image processing unit, and an image display unit configured to display an image of the absorbent article after processing, when a failure location of the absorbent article is detected by the failure detection unit.

17 Claims, 8 Drawing Sheets

(56) References Cited

FOREIGN PATENT DOCUMENTS

| JP | 2003-166810 | 6/2003 |
| WO | WO 2004/014277 A2 | 2/2004 |

OTHER PUBLICATIONS

International Search Report based on corresponding PCT application No. PCT/JP2012/004259 dated Aug. 7, 2012 (1 pg).

European extended Search Report from corresponding European Application No. 12807625.4 dated Nov. 6, 2014 (5 pgs).

Chinese Office Action and English translation from corresponding Chinese Application No. 201280031559.X dated Jun. 12, 2015 (13 pgs).

Taiwanese Office Action and English translation from corresponding Taiwanese Application No. 201280031559.X dated Jun. 12, 2015 (13 pgs).

Taiwanese Examination Report and English translation from corresponding Taiwanese Application No. 101123267 dated Sep. 16, 2015 (11 pgs).

Japanese Official Action and English translation from corresponding Japanese Application No. 2011-147783 dated Oct. 31, 2015 (7 pgs).

* cited by examiner

FAILURE DETECTION SYSTEM AND FAILURE DETECTION METHOD

RELATED APPLICATION

This application is a 35 U.S.C. §371 national phase filing of International Patent Application No. PCT/JP2012/004259, filed Jun. 29, 2012, through which and to which priority is claimed under 35 U.S.C. §119 to Japanese Patent Application No. 2011-147783, filed Jul. 1, 2011.

TECHNICAL FIELD

The present invention relates to a failure detection system and a failure detection method used in a manufacturing line of an absorbent article having a plurality of steps for a conveyed continuous web.

BACKGROUND ART

Conventionally, an absorbent article such as a disposable diaper is generally manufactured by using a manufacturing line in which an absorber and an elastic member (for example, a polyurethane fiber) are arranged sequentially on a continuous web conveyed by a belt conveyor, for example, and the manufacturing line includes a step of folding and a step of cutting the continuous web.

In order to check the manufacturing status of an absorbent article thus manufactured through a plurality of steps, an imaging system in which a camera is installed at a plurality of positions on the manufacturing line, and real-time images of the absorbent article being manufactured are acquired is known (for example, PTL 1). According to such an imaging system, if a failure location exists in an absorbent article being manufactured, the existence of the failure location can be detected promptly.

CITATION LIST

Patent Literature

PTL 1: Japanese Unexamined Patent Application Publication (Translation of PCT Application) No. 2002-535040 (Page No. 20 and 21, FIG. 1)

SUMMARY OF INVENTION

Technical Problem

According to the aforementioned conventional imaging system, because a camera is installed at a plurality of positions on the manufacturing line, the existence of a failure location in an absorbent article being manufactured can be detected promptly. However, there was a problem in that beyond a certain probability, it is difficult to speculate the steps in which the failure locations occurred. That is, the problem with the conventional imaging system is that it is difficult to check the overall status of the manufacturing line, and the steps in which a processing failure of the absorbent article being manufactured occurred cannot be identified easily.

Therefore, the present invention has been developed in view of the above-mentioned status, and an object thereof is to provide a failure detection system and a failure detection method by which it is possible to detect a processing failure of an absorbent article on a manufacturing line, and also to promptly identify the step in which the processing failure has occurred.

Solution to Problem

The present invention is summarized in that a failure detection system used in a manufacturing line of an absorbent article having a plurality of steps for a conveyed continuous web, the system comprising: an image processing unit for acquiring a morphological image illustrating a morphology of the absorbent article after processing of the absorbent article, in each of the said steps; a failure detection unit configured to detect the existence of a failure location of the absorbent article after processing, based on the morphological image acquired by the image processing unit; and an image display unit configured to display an image of the absorbent article after processing, when a failure location of the absorbent article is detected by the failure detection unit.

Advantageous Effect of Invention

According to one characteristic of the present invention, a failure detection system and a failure detection method by which it is possible to detect a processing failure of an absorbent article on a manufacturing line, and also to promptly identify the step in which the processing failure has occurred can be provided.

DESCRIPTION OF EMBODIMENTS

Next, an embodiment of a failure detection system according to the present invention is explained with reference to drawings. In the following description of the drawings, the same or similar reference numerals are used to designate the same or similar parts. It will be appreciated that the drawings are schematically shown and the ratio and the like of each dimension may be different from the real ones.

Accordingly, specific dimensions should be determined in consideration of the explanation below. Moreover, among the drawings, the respective dimensional relations or ratios may differ.

(1) Schematic Configuration of Manufacturing Line

Figure 1:
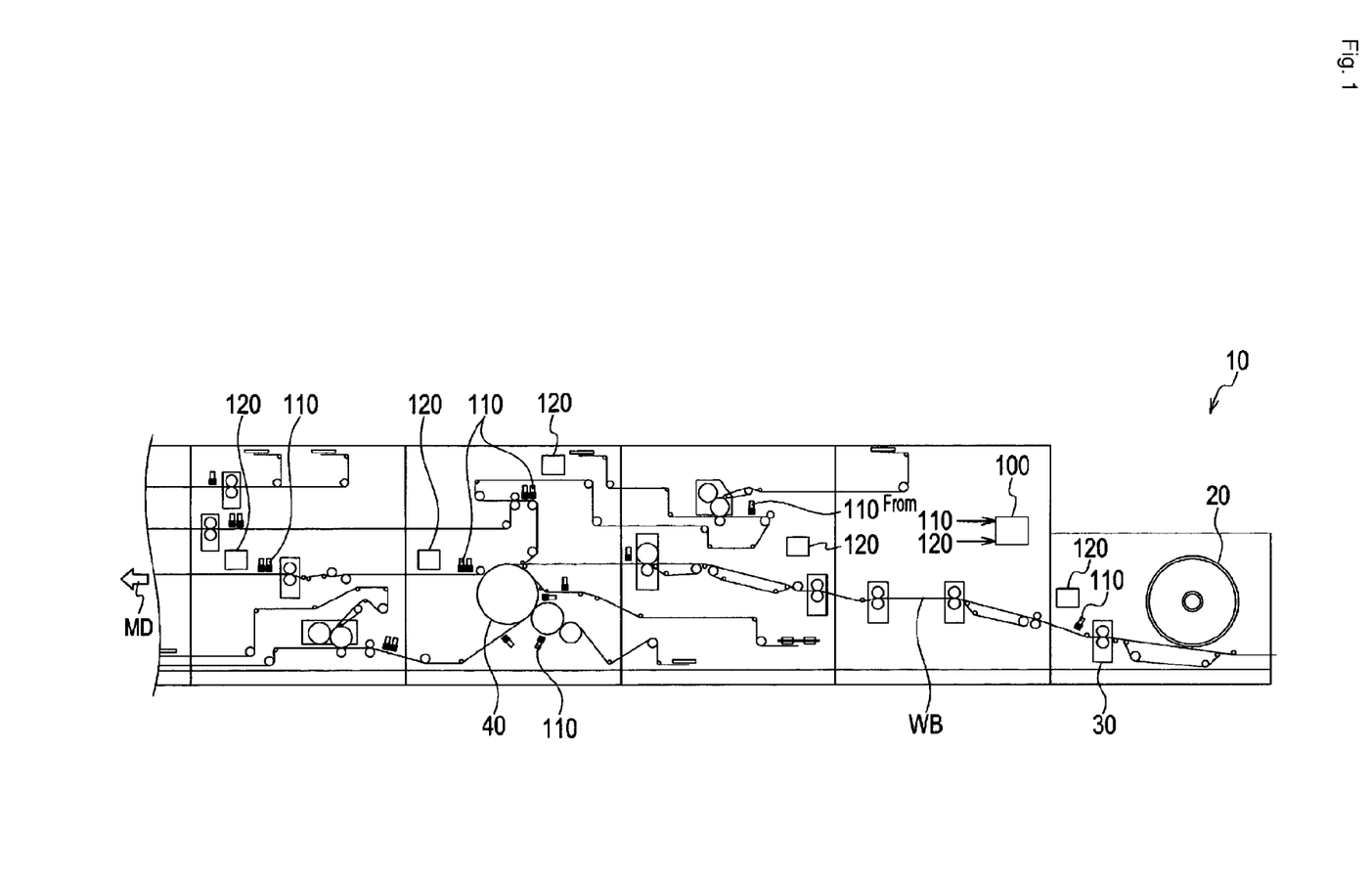
FIG. 1 is a schematic diagram showing the partial configuration of a manufacturing line 10 of an absorbent article according to an embodiment of the present invention.

FIG. 1 is a schematic diagram showing the partial configuration of a manufacturing line 10 of an absorbent article according to the present embodiment.

Figure 5:
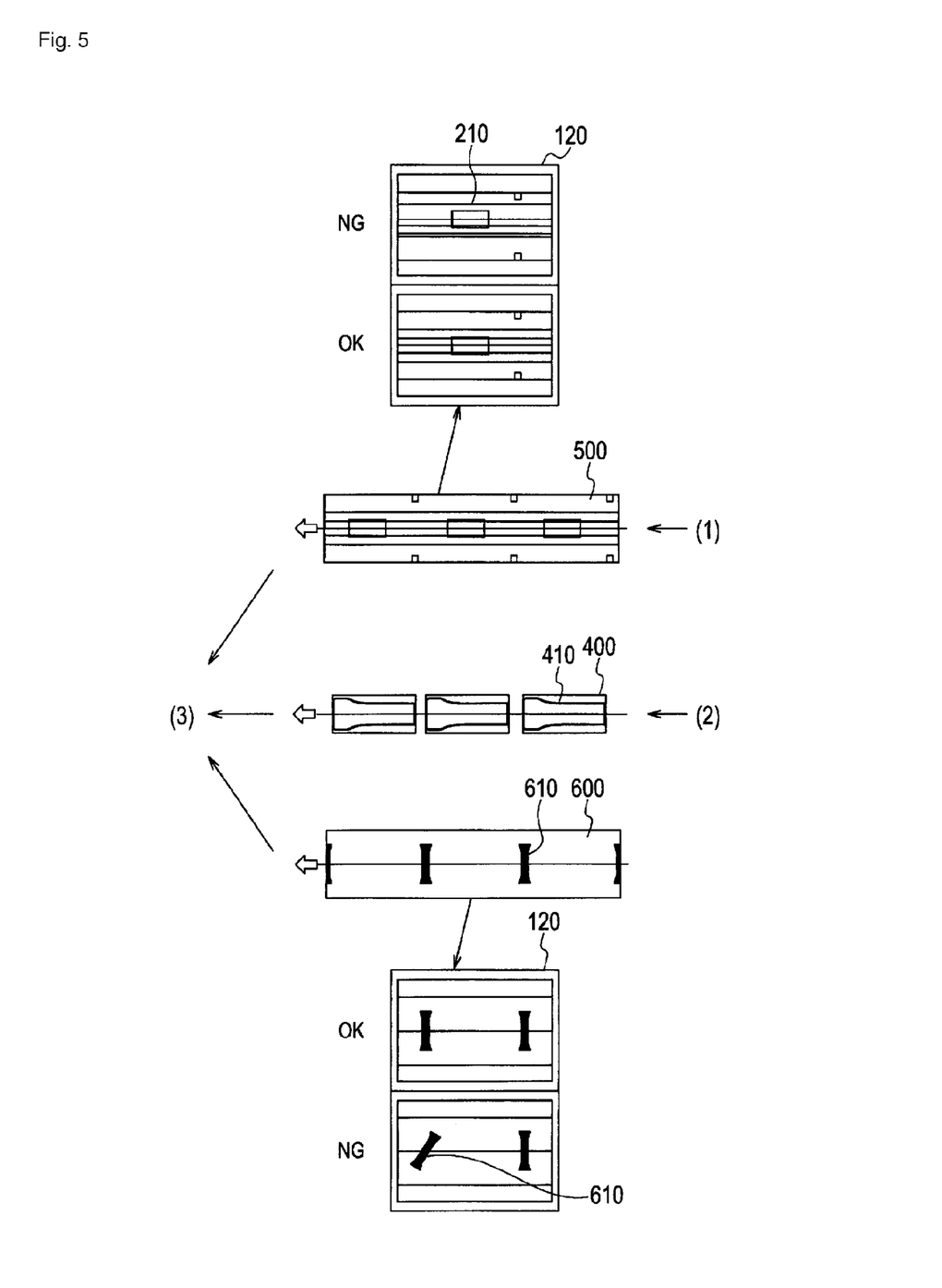
FIG. 5 is a diagram illustrating a failure detection example of the absorbent article PD in a midstream step of the manufacturing line 10 according to the embodiment of the present invention.

The manufacturing line 10 is configured from a plurality of processing devices, which are not shown in FIG. 1 but can be referenced in FIG. 5, configured to manufacture the absorbent article, specifically, an absorbent article PD (not shown in FIG. 1, see FIG. 7), not shown in FIG. 1, see FIG. 5, having an absorber for absorbing liquids, such as a disposable diaper, a sanitary napkin, and a panty liner. Note that in the present embodiment, an open-type disposable diaper having a fastening tape (side tape) to enable attachment and detachment of the front waistline portion and the back waistline portion is manufactured.

The manufacturing line 10 conveys a continuous web WB, which is a continuous body such as a nonwoven fabric and a resin film, towards a machine direction MD, and includes a plurality of steps for the conveyed continuous web WB. Specifically, the manufacturing line 10 finally manufactures the absorbent article PD by folding and cutting the continuous web WB while conveying the continuous web WB.

The manufacturing line 10 includes an absorber laminating drum 20, a plurality of processing devices 30, and a main drum 40.

The absorber laminating drum 20 is installed in an upstream step of the manufacturing line 10, and is configured to laminate a continuous body of an absorber 410 (not shown in FIG. 1, see FIG. 5) provided on each absorbent article PD, on the conveyed continuous web WB. The absorber 410 is configured from pulp and an absorbent polymer.

A plurality of the processing devices 30 are provided on the manufacturing line 10. The processing devices 30 include a flat press element for performing flat pressing on the object to be processed (such as the absorber 410) on the continuous web WB, a heat press element for performing heat pressing, an emboss element for performing embossing, a cutter element for cutting the object to be processed, a heat seal element for joining the object to be processed, and a folding element for folding down the object to be processed.

The main drum 40 glues together a plurality of objects to be processed, specifically, the absorber, the continuous web WB of the center topsheet and the back film, and elastic members such as the leg gathers, leg side gathers, and waist gathers, into a single body.

Furthermore, the manufacturing line 10 is equipped with a failure detection system 100. The failure detection system 100 includes a plurality of cameras 110 and a plurality of image monitors 120 used in the manufacturing line 10.

The cameras 110 are provided between 5 and 10 cm behind the respective exit of the manufacturing step configuring the manufacturing line 10. A location where two cameras 110 are displayed together implies that two cameras are provided in parallel in a crossing direction perpendicular to the machine direction MD (conveyance direction) on the continuous web WB in order to shoot the conveyed continuous web WB specifically, the absorbent article PD).

A plurality of the image monitors 120 are provided at appropriate positions on the manufacturing line 10. The positions of the image monitors 120 are not particularly restricted, however, in order for the operator to be able to quickly check the status of the continuous web WB (absorbent article PD) in each step, the image monitors 120 are provided at appropriate positions in view of the number of the cameras 110.

(2) Functional Block Configuration of the Failure Detection System

Figure 2:
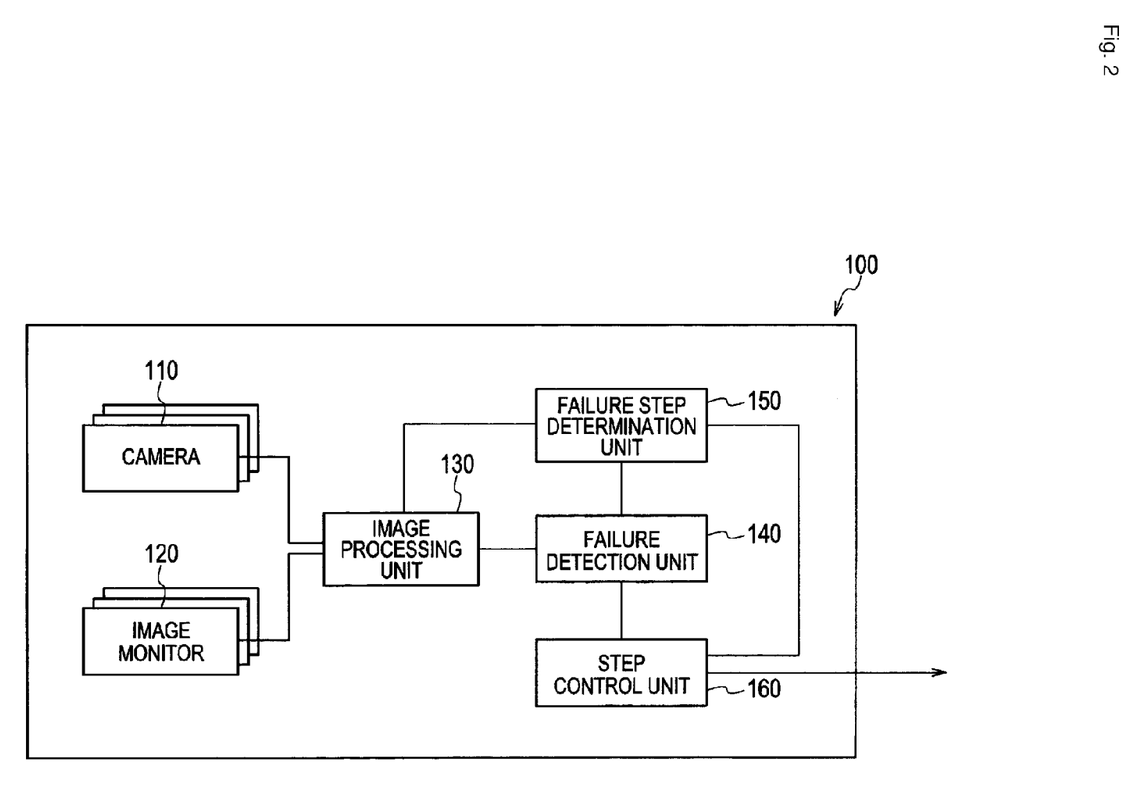
FIG. 2 is a functional block configuration diagram of a failure detection system 100 according to the embodiment of the present invention.

FIG. 2 is a functional block configuration diagram of the failure detection system 100. As shown in FIG. 2, the failure detection system 100 is equipped with the camera 110, the image monitor 120, an image processing unit 130, a failure detection unit 140, a failure step determination unit 150, and a step control unit 160.

The camera 110 is configured to shoot the conveyed continuous web WB (specifically, the absorbent article PD), and acquire morphological images of the absorbent article PD. Depending on the conveyance velocity of the continuous web WB, the camera 110 shoots the continuous web WB at a high speed (for example, at an interval of a few tens of milliseconds), and outputs the shot image data to the image processing unit 130.

The image monitor 120 is configured to display the image data output from the image processing unit 130. Particularly, when a failure location of the absorbent article PD is detected by the failure detection unit 140, the image monitor 120 displays the morphological image of the absorbent article PD after processing. In the present embodiment, the image monitor 120 configures an image display unit. An LCD, for example, on which color display is possible can be used as the image monitor 120.

Furthermore, the image monitor 120 can superimpose and display a plurality of morphological images of the absorbent article PD corresponding to each of the plurality of steps, or can display the plurality of morphological images side by side. Additionally, the image monitor 120 can display the morphological images of the absorbent article PD while sequentially switching the morphological images at a predetermined interval.

Furthermore, the image monitor 120 can superimpose and display a plurality of morphological images of the same absorbent article PD acquired by a plurality of cameras 110 arranged in different steps. This enables the operator to quickly determine the existence of a failure in the absorbent article PD, as well as the step in which the failure has occurred.

The image processing unit 130 is configured to acquire the plurality of morphological images of the absorbent article PD acquired by the plurality of cameras 110, and perform a process using the data of the acquired morphological images. Specifically, the image processing unit 130 digitally processes the data of the acquired morphological images, and compares the data with the data of the already-stored morphological images of the absorbent article PD during manufacturing.

The image processing unit 130 outputs the data of the acquired morphological images, and the data of the already-stored morphology of the absorbent article PD during manufacturing, to the failure detection unit 140. Furthermore, the image processing unit 130 outputs the data of the acquired morphological images to the image monitor 120.

Based on the morphological images acquired by the image processing unit 130, the failure detection unit 140 is configured to detect the existence of a failure location of the absorbent article PD after processing. Specifically, the failure detection unit 140 compares the data of the morphological images of the absorbent article PD acquired by the camera 110 with the data of the already-stored morphology of the absorbent article PD during manufacturing, and determines the existence of a difference in the morphology, and whether or not the difference, if present, is within the already-stipulated permissible range.

By determining that the absorbent article PD being manufactured has a failure when the difference is not within the permissible range, the failure detection unit 140 detects a failure location of the absorbent article PD. By performing such a determination, the failure detection unit 140 can determine whether or not the morphology of the absorbent article PD is normal, and whether or not any foreign substances are added in the absorbent article PD.

When a failure location of the absorbent article PD is detected by the failure detection unit 140, the failure step determination unit 150 determines the step that is the cause of the failure location of the absorbent article PD by comparing the morphological images of each of the plurality of steps acquired by the image processing unit 130. Specifically, the failure step determination unit 150 is configured to determine the existence of a failure location of the absorbent article PD at each position where a camera 110 is provided (shooting position), and when a failure location is not detected in the morphological image of the absorbent article PD in an upstream step from the position where a failure location is detected, the failure step determination unit determines that the cause of the failure lies between the step in which the failure location is not detected, and the step in which the failure location is detected, which is positioned downstream from the step in which the failure location is not detected.

More specifically, the failure step determination unit 150 compares the morphological image of a first step (for example, the step of laminating the absorber on the continuous web WB) included in the plurality of steps and the morphological image of a second step (for example, pasting together the absorber, the center topsheet, and the back film) provided at the downstream side of the conveyance direction from the first step. Additionally, by determining that the cause lies between the first step and the second step when a failure location is not detected in the morphological image of the absorbent article PD in the first step, and a failure location is detected in the second step, the failure step determination unit 150 determines the step that is the cause of the failure location of the absorbent article PD. Other steps may also be interposed between the first step and the second step.

It is desired that the failure step determination unit 150 determine the step that is the cause of the failure location of the absorbent article PD by comparing the morphological image of the first step (for example, the step of laminating the absorber on the continuous web WB) and the morphological image of the second step (for example, the step of flat-pressing the continuous web WB on which the absorber is laminated) provided "immediately after" the first step at the downstream side of the conveyance direction. As a result of such a determination by the failure step determination unit 150, the step that is the cause of the failure location of the absorbent article PD can be determined more certainly.

Based on the failure location of the absorbent article PD that is detected by the failure detection unit 140, and the step determined by the failure step determination unit 150, the step control unit 160 controls the parameters that can be changed in the step. Specifically, based on the failure location of the absorbent article PD that is detected by the failure detection unit 140, and the morphological image processed by the image processing unit 130, the step control unit 160 is configured to control the supply speed and timing of various members supplied to the main drum 40. For example, based on the morphological image processed by the image processing unit 130, when the supply speed (timing) of a specific member supplied to the main drum 40 is fast (or slow), the step control unit 160 controls the parameters such as the rotation speed of the related motor (not shown in the figure) so as to slow down (speed up) the supply speed of the member.

(3) Operation of the Failure Detection System

Figure 3:
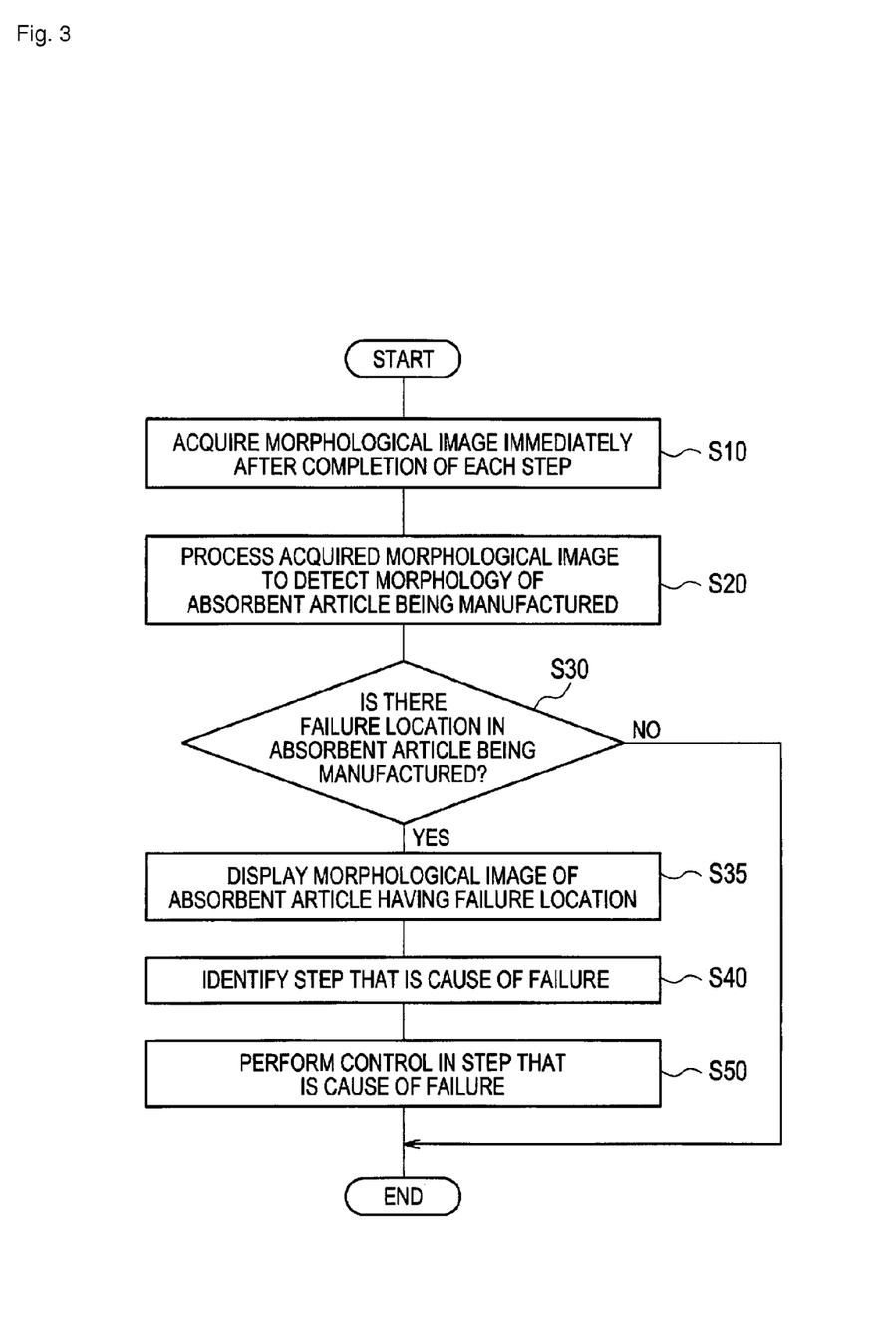
FIG. 3 is a diagram illustrating a failure detection operation flow of an absorbent article PD by the failure detection system 100 according to the embodiment of the present invention.

FIG. 3 illustrates the failure detection operation flow of the absorbent article PD by the failure detection system 100. As shown in FIG. 3, the failure detection system 100 acquires the morphological images of the continuous web WB (absorbent article PD) immediately after the completion of each step, by using the camera 110 (S10).

The failure detection system 100 processes the data of the acquired morphological images, and acquires the morphological images of the absorbent article PD during manufacturing (S20).

Based on the acquired morphological images, the failure detection system 100 determines whether or not any failure location exists in the absorbent article PD being manufactured (S30). Specifically, by comparing the data of the morphological images of the absorbent article PD acquired by the camera 110 with the data of the already-stored morphology of the absorbent article PD during manufacturing, the failure detection system 100 determines whether or not a failure location exists in the absorbent article PD being manufactured.

Based on the morphological images acquired from the plurality of cameras 110, the failure detection system 100 displays the morphological image having a failure location on the image monitor 120 (S35).

Based on the morphological images acquired from the plurality of cameras 110, the failure detection system 100 identifies the step that could be a cause of the detected failure location (S40). Specifically, by comparing the morphological image of a step (first step), which is acquired by a specific camera 110 and the morphological image of a step (second step) provided immediately after the first step, which is acquired by another camera 110, the failure detection system 100 determines the step that is the cause of the failure location of the absorbent article PD.

When the morphological image of the first step is normal and the morphological image of the second step is abnormal, the failure detection system 100 determines the first step as the step that is the cause of the failure location of the absorbent article PD. The failure detection system 100 performs such a determination for each step across the entire manufacturing line 10, and determines the step that is the cause of the failure location of the absorbent article PD.

Furthermore, when the failure detection system 100 determines the step that is the cause of the failure location of the absorbent article PD, the failure detection system 100 may superimpose and display the plurality of morphological images of the absorbent article PD corresponding to each of the plurality of steps (first step and second step).

The failure detection system 100 performs control in the step that is the cause of the failure location of the absorbent article PD (S50). Specifically, the failure detection system 100 controls the parameters that can be changed in the step that is the cause of the failure location of the absorbent article PD. For example, as described above, when the supply speed (timing) of a specific member supplied to the main drum 40 is fast (or slow), the failure detection system 100 controls the parameters such as the rotation speed of the related motor (not shown in the figure) so as to slow down (speed up) the supply speed of the member.

(4) Failure Detection Example

Figure 4:
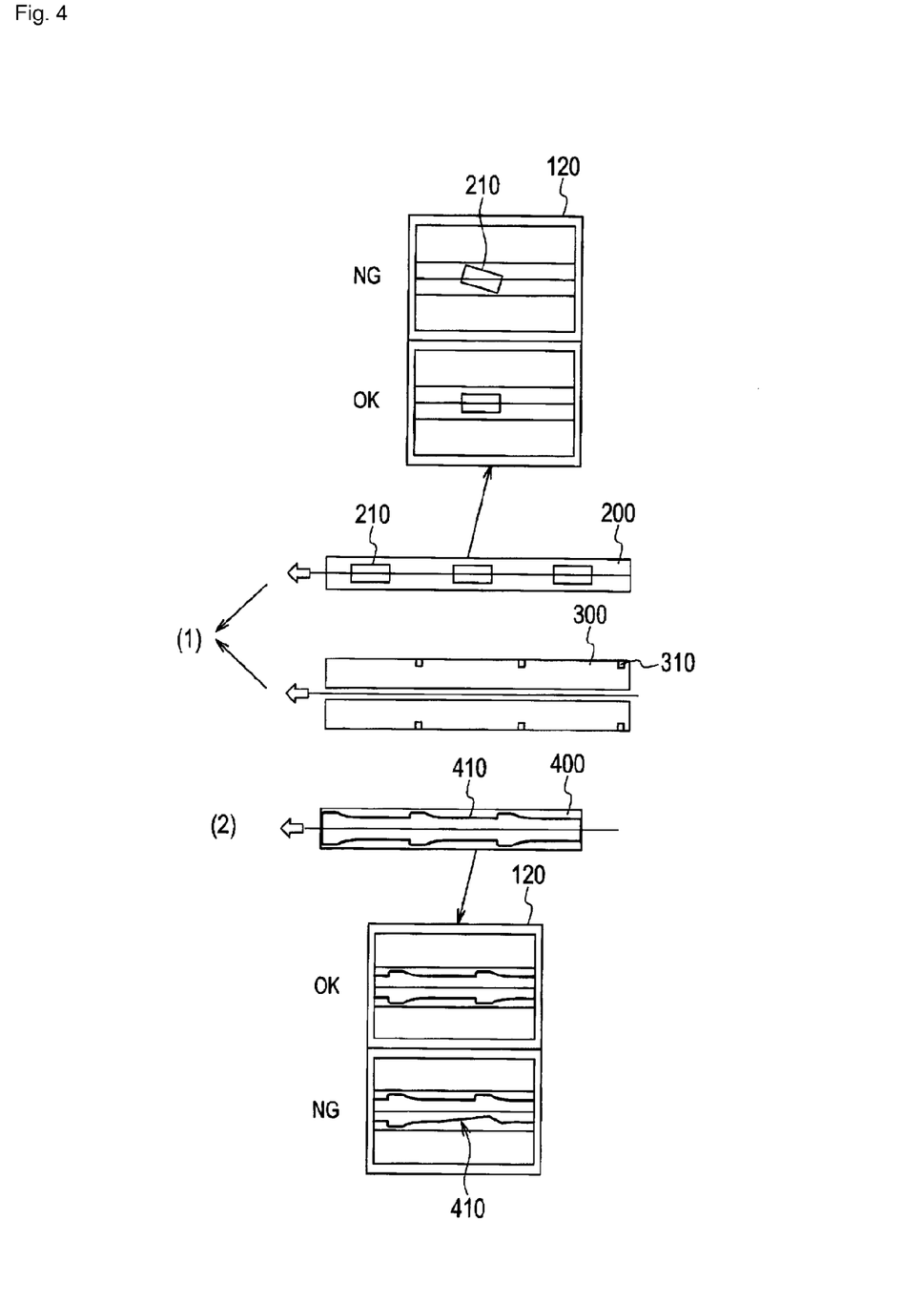
FIG. 4 is a diagram illustrating a failure detection example of the absorbent article PD in an upstream step of the manufacturing line 10 according to the embodiment of the present invention.
Figure 6:
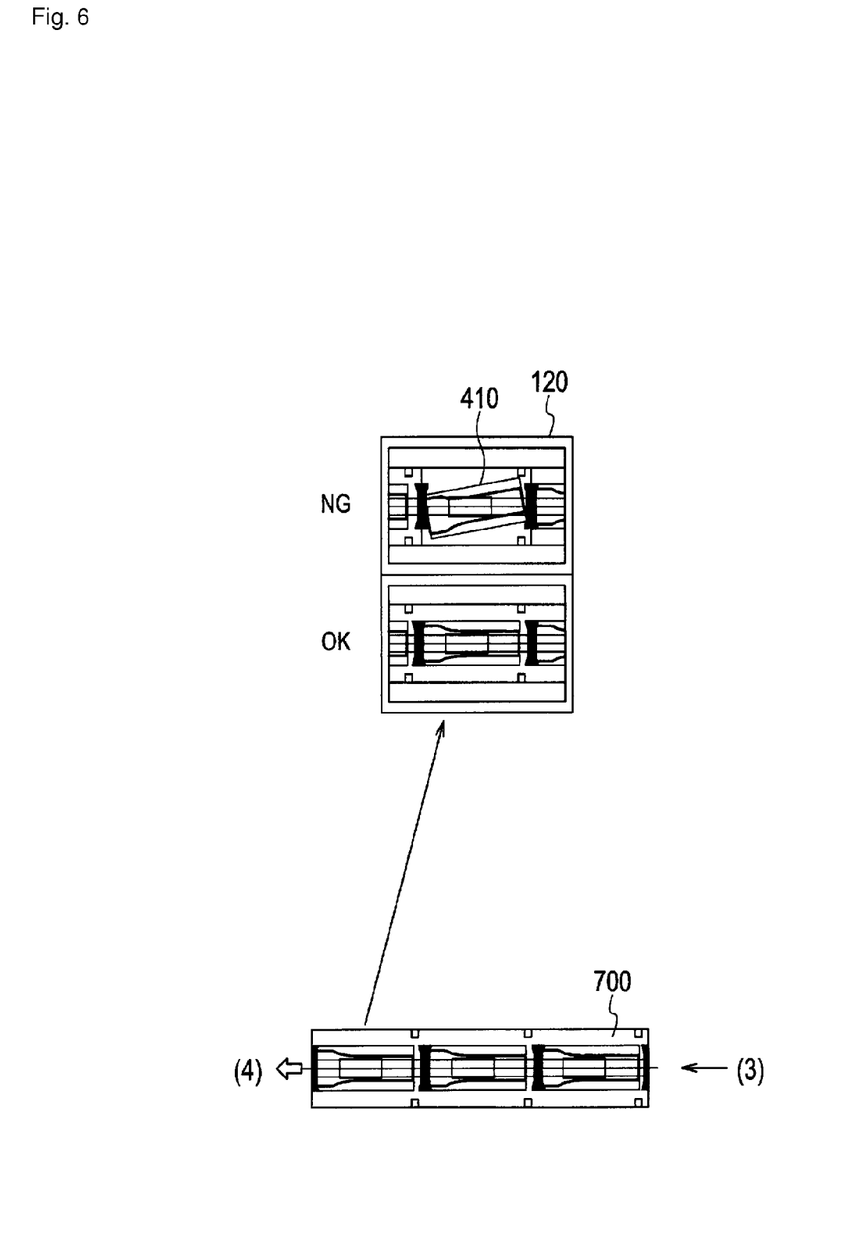
FIG. 6 is a diagram illustrating a failure detection example (1) of the absorbent article PD in a downstream step of the manufacturing line 10 according to the embodiment of the present invention.
Figure 7:
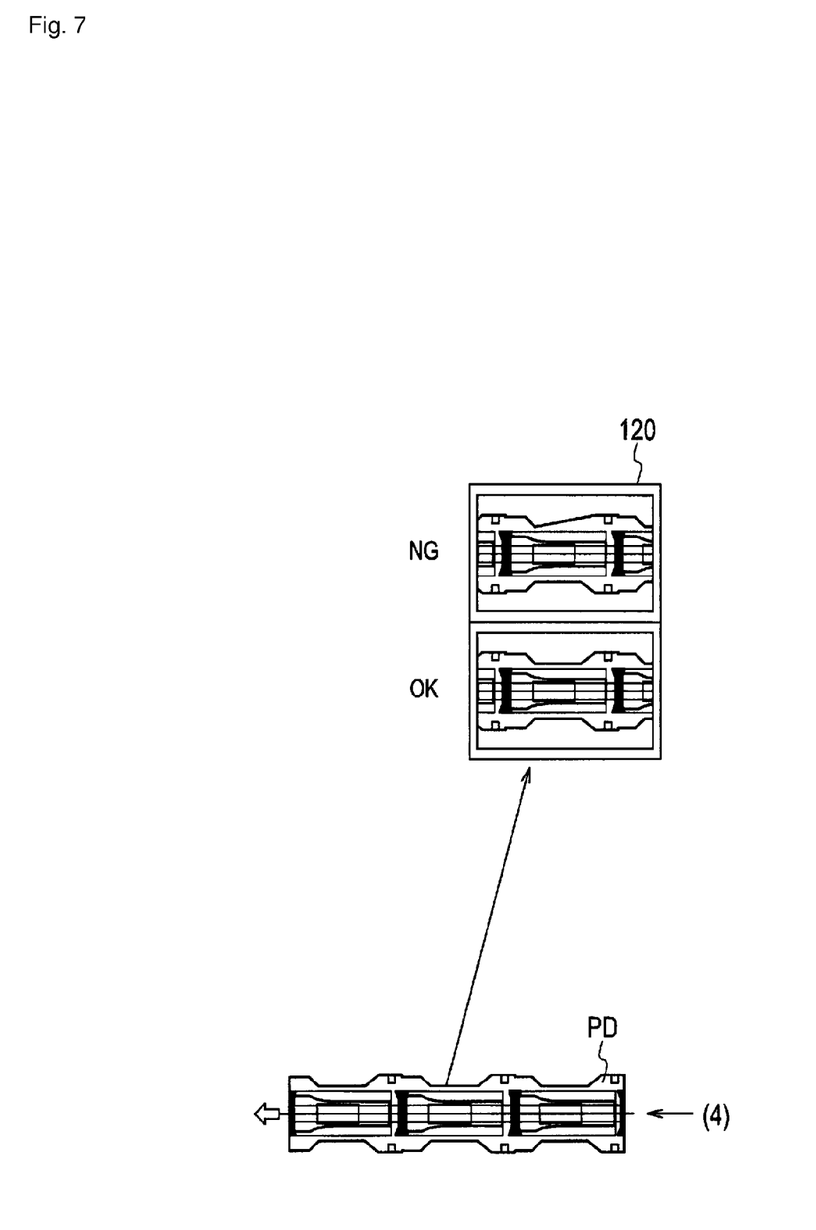
FIG. 7 is a diagram illustrating a failure detection example (2) of the absorbent article PD in a downstream step of the manufacturing line 10 according to the embodiment of the present invention.
Figure 8:
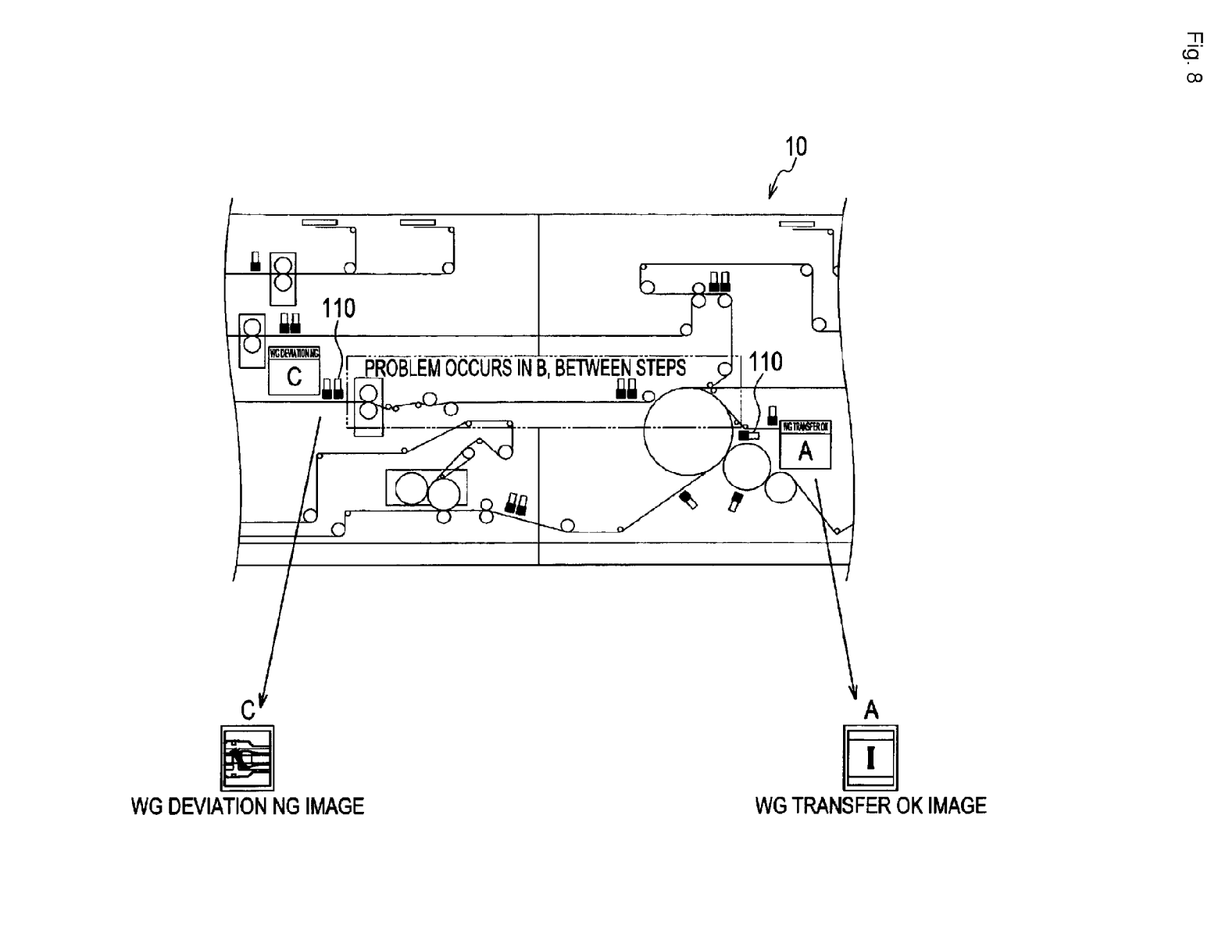
FIG. 8 is a diagram illustrating a determination result example of a failure location of the manufacturing line 10 according to the embodiment of the present invention.

FIG. 4 through FIG. 8 illustrate a failure detection example of the absorbent article PD. Specifically, FIG. 4 illustrates a failure detection example of the absorbent article PD in an upstream step of the manufacturing line 10, and FIG. 5 illustrates a failure detection example of the absorbent article PD in a midstream step of the manufacturing line 10. Furthermore, FIG. 6 and FIG. 7 illustrate a failure detection example of the absorbent article PD in a downstream step of the manufacturing line 10. FIG. 8 is a diagram illustrating a determination result example of a failure location of the manufacturing line 10.

FIG. 4 illustrates that a center topsheet 200 including a cushion sheet 210, a sidesheet 300 including a side tape 310, and an absorber line 400 including an absorber 410 are conveyed in an upstream step of the manufacturing line 10. Each of the center topsheet 200, the sidesheet 300, and the absorber line 400 is a member configuring an open-type disposable diaper. The center topsheet 200 and the sidesheet 300 are converged into a single body ((1) in the figure).

The image monitor 120 of FIG. 4 illustrates an example of a morphological image when there is no failure location (OK in the figure) in the absorbent article PD, and when there is a failure location (NG in the figure) in the absorbent article PD. As shown in FIG. 4, the image monitor 120 displays the morphological image of the state when the cushion sheet 210 is arranged at an inclination, and the state when the absorber 410 is chipped off (folded).

FIG. 5 illustrates that a sidesheet/center topsheet laminate 500 in which the center topsheet 200 and the sidesheet 300 are pasted together, the absorber line 400 cut into a predetermined size, and a backsheet 600 including waist gathers 610 are conveyed in a midstream step of the manufacturing line 10.

The sidesheet/center topsheet laminate 500 is obtained by pasting together the center topsheet 200 and the sidesheet 300 (see (1) in FIG. 4 and FIG. 5). The absorber line 400 is conveyed from an upstream step (see (2) in FIG. 4 and FIG. 5), and is cut in a midstream step by using a cutter element (not shown in the figure). The absorber line 400, the sidesheet/center topsheet laminate 500, and the backsheet 600 are converged into a single body ((3) in the figure).

The image monitor 120 of FIG. 5 also illustrates an example of a morphological image when there is no failure location (OK in the figure) in the absorbent article PD, and when there is a failure location (NG in the figure) in the absorbent article PD. As shown in FIG. 5, the image monitor 120 displays a morphological image of the state when the cushion sheet 210 is arranged by deviating in the crossing direction perpendicular to the machine direction MD, and the state when the waist gathers 610 are arranged at an inclination.

FIG. 6 illustrates that a laminated body 700 (see (3) in the figure) in which the absorber line 400, the sidesheet/center topsheet laminate 500, and the backsheet 600 are set as a single body is conveyed in a downstream step of the manufacturing line 10. As shown in FIG. 6, the image monitor 120 displays a morphological image of the state when the absorber 410 is arranged at an inclination.

Furthermore, FIG. 7 illustrates that the absorbent article PD (open-type disposable diaper) in which the sides of the laminated body 700 are cut in the shape of the product is conveyed in a further downstream step of the manufacturing line 10. As shown in FIG. 7, the image monitor 120 displays a morphological image of the state when the sides of the laminated body 700 could not be cut into the prescribed shape.

Furthermore, the example shown in FIG. 8 illustrates the failure step determined based on the morphological images acquired by the camera 110 provided at the position "A" (waist gathers (WG) transfer step) of the manufacturing line 10 and the camera 110 provided at the position "C" (cutting step) of the manufacturing line 10. At position "A" of the manufacturing line 10, an image in which the transfer of the waist gathers is good (OK) is displayed on the image monitor 120, and at position "C" of the manufacturing line 10, a problematic (NG) image in which a deviation occurs in the waist gathers is displayed on the image monitor 120.

Thus, when the absorbent article PD is good at position "A" of the manufacturing line 10, and the absorbent article PD is problematic at position "C" of the manufacturing line 10, it is determined by the failure step determination unit 150 that a problem has occurred in the region "B", between the steps "A" and "C", which is the cause of the failure location, as shown in FIG. 8.

(5) Operation and Effect

According to the failure detection system 100 of the present embodiment, the existence of a failure location in the absorbent article PD after processing is detected based on the morphological images of the absorbent article PD acquired by the image processing unit 130. When a failure location is detected in the absorbent article PD by the failure detection unit, an image of the absorbent article PD after processing is displayed on the image monitor 120.

Therefore, the operator working at the manufacturing line 10 can promptly check the morphological images of the absorbent article PD immediately after each step, and can promptly identify the step that is the cause of the failure and promptly take action to resolve the failure. That is, according to the failure detection system 100, the operator can not only detect the occurrence of a processing failure of the absorbent article PD on the manufacturing line 10, but also promptly identify the step in which the processing failure has occurred.

In the present embodiment, because the morphological images of each of the plurality of steps acquired by the image processing unit 130 are compared by the failure detection unit 140, the step that is the cause of the failure location of the absorbent article PD is determined. Specifically, by comparing the morphological image of the first step and the morphological image of the second step provided immediately after the first step at the downstream side of the conveyance direction, the failure step determination unit 150 determines the step that is the cause of the failure location of the absorbent article PD.

Therefore, because the failure detection system 100 itself can determine the step in which the processing failure has occurred and can display the morphological images related to the step on the image monitor 120, the operator can more quickly identify the step in which the processing failure has occurred, by intensively checking the step determined by the failure detection system 100. That is, because the failure detection system 100 provides such a function, self-diagnosis of the manufacturing line 10 is enabled.

Furthermore, in the present embodiment, a plurality of morphological images corresponding to each of the plurality of steps can be superimposed and displayed on the image monitor 120. Therefore, by comparing the images, the operator can easily check the state of failure of the absorbent article PD, and can contribute to a fast determination and action for the step in which the processing failure has occurred.

In the present embodiment, based on the step determined by the failure step determination unit 150, the step control unit 160 can control the parameters that can be changed in the step. Therefore, the processing failure of the absorbent article PD can be resolved automatically and promptly.

(6) Other Embodiments

As described above, the present invention is disclosed through the above embodiments. However, it should not be interpreted that the statements and drawings constituting a part of the present disclosure limit the present invention. From this disclosure, a variety of alternate embodiments, examples, and applicable techniques will become apparent to one skilled in the art.

For example, in the aforementioned embodiment, based on the failure location of the absorbent article PD detected by the failure detection unit 140, and the step determined by the failure step determination unit 150, the step control unit 160 controlled the parameters that can be changed in the step, however, such a function need not necessarily be provided in the failure detection system 100.

In the aforementioned embodiment, the plurality of morphological images corresponding to each of the plurality of steps could be superimposed and displayed on the image monitor 120, however, such a function need not necessarily be provided in the failure detection system 100.

In the aforementioned embodiment, the morphological images of the first step and the second step provided "immediately after" the first step at the downstream side of the conveyance direction were compared, however, the second step need not necessarily be provided immediately after the first step.

In the aforementioned embodiment, the failure step determination unit 150 determined the step that was the cause of the failure location of the absorbent article PD, however, such a determination need not necessarily be performed. Alternatively, when the failure step determination unit 150 cannot determine the step that is the cause of the failure location, the options of a plurality of steps may be displayed. Additionally, the determination of the failure step may be taken by the operator based on the failure location of the absorbent article PD detected by the failure detection unit 140.

As described above, needless to say, the present invention includes various embodiments and the like not described here. Therefore, the technical range of the present invention is to be defined only by the inventive specific matter according to the adequate claims from the above description.

REFERENCE SIGNS LIST

10 Manufacturing line
20 Absorber laminating drum
30 Processing device
40 Main drum
100 Failure detection system
110 Camera
120 Image monitor
130 Image processing unit
140 Failure detection unit
150 Failure step determination unit
160 Step control unit
200 Center topsheet
210 Cushion sheet
300 Sidesheet
310 Side tape
400 Absorber line
410 Absorber
500 Sidesheet/center topsheet laminate
600 Backsheet
610 Waist gathers
700 Laminated body
PD Absorbent article
WB Continuous web

The invention claimed is:

1. A failure detection system used in a manufacturing line of absorbent articles, the manufacturing line having a plurality of processing steps for a conveyed continuous web, the failure detection system comprising:
   an image processing unit for acquiring morphological images illustrating morphologies of entire ones of the absorbent articles after processing of the absorbent articles in each of the said processing steps;
   a failure detection unit that detects the existence of a failure location of the absorbent articles after processing, based on the morphological images acquired by the image processing unit; and
   an image display unit that displays images of the absorbent articles after processing, when a failure location of an absorbent article is detected by the failure detection unit,
   wherein the failure detection unit determines if a processing step has caused a processing failure by comparing subsequent acquired morphological images of a processed absorbent article with precedingly obtained morphological images of the processed absorbent article.

2. The failure detection system according to claim 1, further comprising the failure step determination unit compares morphological images acquired after each of the plurality of processing steps, which are acquired by the image processing unit, when the failure detection unit detects a failure location of the absorbent article.

3. The failure detection system according to claim 2, wherein the failure step determination unit compares an acquired morphological image after a first processing step included in the plurality of processing steps and an acquired morphological image after a second processing step provided at a downstream side of a conveyance direction from the first processing step.

4. The failure detection system according to claim 3, wherein the failure step determination unit compares an acquired morphological image after the first processing step and an acquired morphological image after the second processing step provided immediately after the first processing step at a downstream side in the conveyance direction.

5. The failure detection system according to claim 2, wherein the image display unit superimposes and displays a plurality of the acquired morphological images corresponding to each of the plurality of steps.

6. The failure detection system according to claim 5, further comprising a step control unit for controlling a parameter that can be changed in the step determined by the failure step determination unit, based on a failure location of an absorbent article detected by the failure detection unit, and the processing step determined by the failure step determination unit.

7. The failure detection system according to claim 2, further comprising a step control unit for controlling a parameter that can be changed in the step determined by the failure step determination unit, based on a failure location of an absorbent article detected by the failure detection unit, and the processing step determined by the failure step determination unit.

8. The failure detection system according to claim 3, wherein the image display unit superimposes and displays a plurality of the acquired morphological images corresponding to each of the plurality of steps.

9. The failure detection system according to claim 8, further comprising a step control unit for controlling a parameter that can be changed in the step determined by the failure step determination unit, based on a failure location of an absorbent article detected by the failure detection unit, and the processing step determined by the failure step determination unit.

10. The failure detection system according to claim 3, further comprising a step control unit for controlling a parameter that can be changed in the step determined by the failure step determination unit, based on a failure location of an absorbent article detected by the failure detection unit, and the processing step determined by the failure step determination unit.

11. The failure detection system according to claim 4, wherein the image display unit superimposes and displays a plurality of the acquired morphological images corresponding to each of the plurality of steps.

12. The failure detection system according to claim 11, further comprising a step control unit for controlling a parameter that can be changed in the step determined by the failure step determination unit, based on a failure location of an absorbent article detected by the failure detection unit, and the processing step determined by the failure step determination unit.

13. The failure detection system according to claim 4, further comprising a step control unit for controlling a parameter that can be changed in the step determined by the failure step determination unit, based on a failure location of an absorbent article detected by the failure detection unit, and the processing step determined by the failure step determination unit.

14. The failure detection system according to claim 1, wherein the image display unit superimposes and displays a plurality of acquired morphological images corresponding to each of the plurality of steps.

15. The failure detection system according to claim 14, further comprising a step control unit for controlling a parameter that can be changed in the step determined by the failure step determination unit, based on a failure location of an absorbent article detected by the failure detection unit, and the processing step determined by the failure step determination unit.

16. The failure detection system according to claim 1, further comprising a step control unit for controlling a parameter that can be changed in the step determined by the failure step determination unit, based on a failure location of an absorbent article detected by the failure detection unit, and the step determined by the failure step determination unit.

17. A failure detection method used in a manufacturing line of absorbent articles, the manufacturing line having a plurality of processing steps for a conveyed continuous web, the failure detection method comprising:
- a step of acquiring morphological images illustrating morphologies of entire ones of the absorbent articles after processing of the absorbent articles in each of the plurality of processing steps;
- a step of detecting the existence of a failure location of the absorbent articles after processing, based on the acquired morphological images; and
- a step of displaying images of the absorbent articles after processing, when a failure location of an absorbent article is detected,
- wherein the failure detection unit determines if a processing step has caused a processing failure by comparing subsequent acquired morphological images of a processed absorbent article with precedingly obtained morphological images of the processed absorbent article.

* * * * *